(12) United States Patent
Lei et al.

(10) Patent No.: US 7,064,224 B1
(45) Date of Patent: Jun. 20, 2006

(54) ORGANOMETALLIC COMPLEXES AND THEIR USE AS PRECURSORS TO DEPOSIT METAL FILMS

(75) Inventors: Xinjian Lei, Vista, CA (US); Manchao Xiao, San Diego, CA (US); Hareesh Thridandam, Vista, CA (US); Kirk Scott Cuthill, Vista, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 11/051,140

(22) Filed: Feb. 4, 2005

(51) Int. Cl.
*C07F 7/10* (2006.01)
*H01L 21/44* (2006.01)
*C23C 16/00* (2006.01)

(52) U.S. Cl. ............... 556/9; 427/255.28; 427/255.31; 427/587; 427/593; 438/681

(58) Field of Classification Search .................... 556/9; 427/587, 593, 255.28, 255.31; 438/681
See application file for complete search history.

(56) References Cited

U.S. PATENT DOCUMENTS

| 5,314,727 | A | 5/1994 | McCormick et al. |
| 6,753,245 | B1 | 6/2004 | Choi |
| 6,777,565 | B1 | 8/2004 | Choi |
| 2002/0016065 | A1 | 2/2002 | Uhlenbrock et al. |
| 2002/0081381 | A1 | 6/2002 | DelaRosa et al. |
| 2004/0005753 | A1 | 1/2004 | Kostamo et al. |

FOREIGN PATENT DOCUMENTS

WO   WO 2004/046417   6/2004

OTHER PUBLICATIONS

Sharma et al., Applied Organometallic Chemistry, vol. 15, No. 3, pp. 221-226 (2001).*
S. Lim Booyang, et al, Atomic Layer Deposition of Transition Metals, Nature Materials,Nature Publishing Group, vol. 2, 749, 2003.
Eiji Fujii, et al, Low-Temperature Preparation and Properties of Spinel-Type . . . , Jpn. J. Appl. Phys. vol. 32, 1993, pp. 1527-1529.
Sergej Pasko, et al, Synthesis and Molecular Structures of Cobalt(II) . . . , Polyhedron 23, 2004, pp. 735-741.
Shou Gu, et al, Chemical Vapor Deposition of Copper-Cobalt Binary Films, Thin Solid Films 340, 1999, pp. 45-52.
Hwa Sung Rhee, et al, Epitaxial Growth of A (100) CoSi2 Layer From Carbonic . . . , Applied Physics Letters, vol. 74, No. 7, pp. 1003-1005.
D.G. Anderson, et al, Chemical Vapor Deposition of Metals and Metal Silicides . . . , Jour. of Organometallic Chem., 437, 1992, pp. C7-C12.

Laurent Brissonneau, et al, MOCVD-Processed Ni Films From Nickelocene . . . , Chem. Vap. Deposition, 1999, 5, No. 4, pp. 135-142.
Penelope A. Lane, et al, Growth of Iron, Nickel, and Permalloy Thin Films by MOCVD . . . , Chem. Vap. Deposition, 1997, 3, No. 2, pp. 97-101.
Eiji Fujii, et al, Preferred Orientations of NiO Films Prepared by Plasma-Enhanced . . . , Jpn. J. Appl. Phys., vol. 35, 1996, pp. L328-L330.
M. Becht, et al, Nickel Thin Films Grown by MOCVD Using Ni(dmg)2 as Precursor, Journal De Physique IV, 5(C5), 1995, pp. C5-465-C5-472.
B. Fraser, et al, Investigation of [(py)(Et)Co(dmg GaEt2)2] and [Ni(dmg GaEt2)2] . . . , Jour. of Organometallic Chem., 472, 1994, pp. 317-328.
Junghun Chae, et al, Atomic Layer Deposition of Nickel by the Reduction of . . . , Electro. and Solid-State Letters, vol. 5, (6) 2002, pp. C64- C66.
Booyong S. Lim, et al, Synthesis and Characterization of Volatile, Thermally Stable, Reactive Transition Metal Amidinates, Inorganic Chem., 2003, vol. 42: 7951.
Booyong S. Lim, et al, Atomic Layer Depositon of Transition Metals, Nature Materials, Nature Publishing Group, Vo. 2, 2003, pp. 749-754.
Wing-Por Leung, et al, Synthesis and Structural Characterisation of Mono- and bi- nuclear Cobalt . . . , J. Chem. Soc., Dalton Trans., 1997, pp. 779-783.

* cited by examiner

*Primary Examiner*—Porfirio Nazario-Gonzalez
(74) *Attorney, Agent, or Firm*—Geoffrey L. Chase

(57) ABSTRACT

This invention is related to organometallic precursors and deposition processes for fabricating conformal metal containing films on substrates such as silicon, metal nitrides and other metal layers.

The organometallic precursors are N,N'-alkyl-1,1-alkylsilylamino metal complexes represented by the formula:

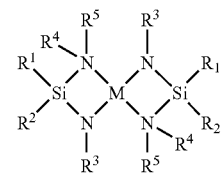

wherein M is a metal selected from Group VIIb, VIII, IX and X, and specific examples include cobalt, iron, nickel, manganese, ruthenium, zinc, copper, palladium, platinum, iridium, rhenium, osmium, and the $R^{1-5}$ can be same or different selected from hydrogen, alkyl, alkoxy, fluoroalkyl and alkoxy, cycloaliphatic, and aryl.

20 Claims, No Drawings

ORGANOMETALLIC COMPLEXES AND THEIR USE AS PRECURSORS TO DEPOSIT METAL FILMS

BACKGROUND OF THE INVENTION

Highly conformal thin films of metals and metal oxides with a thickness of 50 Å or less are attaining increased attention in the fabrication of electronic devices including microelectronics, and magnetic information storage. Typically, these films have been produced by chemical vapor deposition (CVD) and atomic layer deposition (ALD) methods. As component device (i.e., transistors) size shrinks and increased densities of component devices and circuits are patterned, there is considerable need for new types of organometallic precursor compounds that can lead to the fabrication of these types of films by either CVD or ALD methods.

Thermally stable metal amidinates have been used as candidates for producing highly conformal thin films of transition metals. These might be used in producing logic and memory devices. Exemplary metals employed for such metal amidinates include cobalt, vanadium, iron, and nickel.

Metal silicides derived from metals of Groups VIIb, VIII, IX, and X have been shown to be attractive compounds in the electronics field particularly in the manufacture of integrated circuits and micro-electronics. Interest in metal silicides is increasing as device scale-down progresses due to their good thermal and chemical stability, low electrical resistivity, wide processing window and their small lattice mismatch to the silicon crystal lattice, which allows the metal silicide to be grown epitaxially on silicon.

The following patents and articles are representative of organometallic compounds suited for producing conformal thin metal or metal oxide films by CVD and ALD and their use in the electronics industry.

U.S. Pat. No. 6,777,565 B2 and U.S. Pat. No. 6,753,245 B2 disclose the deposition of metal films using organometallic compounds having the formula $(R^1)_m M(PR^2{}_3)_x$ where M is a metal selected from the group consisting of Group VIIb, VIII, IX, or X such as iron, cobalt, nickel, manganese rhodium and so forth. Metal silyl phosphites are also shown and examples include those of the formula $H_2M[(CH_3)_3SiOP(OC_2H_5)_2]_4$, and $M[(CH_3)_3SiOP(OCH_3)_2]_5$.

US 2002/0081381 discloses the formation of cobalt films by alternately reacting bis(acetylacetonato)cobalt with either hydrogen or silane in an ALD process. The cobalt can be used as a glue layer between copper and a diffusion barrier layer such as that from TiN, TaN, and WN to improve the adhesion.

US 2002/0016065 discloses the formation of metal-containing films using organometallic complexes in which the metal center is coordinated with chelating C,N-donor ligands. One of the complexes, illustrated in the Example, $Co\{C(SiMe_3)_2(C_5H_4N)\}_2$, was used to form a cobalt film on a silicon substrate.

WO 2004/046417 A2 and Roy G. Gordon, et al., *Alternate Layer Deposition of Transition Metals*, Nature Materials, vol. 2, 749 (November 2003) disclose the formation of highly conformal thin films by ALD using metal amidinates as an organometallic precursor. Cobalt (II) bis (N,N'-diisopropylacetamidinate, bis(N,N'-tert-butylacetamidinato) manganese and lanthanum tris(N,N'-dissopropyl-2-tert-butylamidinate) are shown as precursors.

BRIEF SUMMARY OF THE INVENTION

This invention is related to organometallic precursors and deposition processes for fabricating conformal metal containing films on substrates such as silicon, metal nitride and other metal layers using these organometallic precursors. Such films have applications ranging from computer chips, optical devices, magnetic information storage, to metallic catalyst coated on a supporting material.

The organometallic precursors are N,N'-alkyl-1,1-alkylsilylamino metal complexes having the formula:

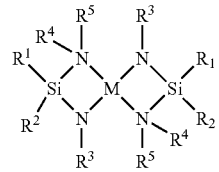

wherein M is a metal selected from Group VIIb, VIII, IX and X, and specific examples of metals include cobalt, iron, nickel, manganese, vanadium, lanthanum, ruthenium, zinc, copper, palladium, platinum, iridium, rhenium, osmium, and the $R^{1-5}$ can be same or different and are selected from hydrogen, alkyl, alkoxy, fluoroalkyl and alkoxy, cycloaliphatic, and aryl groups.

Several advantages can be achieved through these organometallic complexes, particularly, N,N'-alkyl-1,1-alkylsilylamino metal complex precursors, and these include:

an ability to form reactive N,N'-alkyl-1,1-alkylsilylamino metal complexes in good yield;

an ability to produce highly conformal metal thin films suited for use in a wide variety of electrical applications;

an ability to form highly conformal metal oxide thin films suited for use in microelectronic devices;

an ability to enhance the surface reaction between the N,N'-alkyl-1,1-alkylsilylamino metal complex and the surface of a substrate due to the high chemical reactivity of the complexes; and, an ability to tune the physical property of the N,N'-alkyl-1,1-alkylsilylamino metal complex via a change in the R groups on the N,N'-alkyl-1,1-alkylsilylamino metal complex.

DETAILED DESCRIPTION OF THE INVENTION

This invention is related to a class of organometallic complexes, typically N,N'-alkyl-1,1-alkylsilylamino metal complexes, having chelating N,N'-donor ligands, their synthesis and use in deposition processes The general formula of these N,N'-alkyl-1,1-alkylsilylamino metal complexes can be represented as follows: $M\{R^1R^2Si(NR^3)(NR^4R^5))\}_2$ where M is a metal selected from Group VIIb, VIII, IX and X, and specific examples of metals include cobalt, iron, nickel, manganese, ruthenium, zinc, copper, palladium, platinum, iridium, rhenium, osmium. $R^{1-5}$ is selected from the group consisting of hydrogen, alkyl or alkoxy groups, fluoroalkyl and alkoxy groups, aryl and cycloaliphatic groups.

These organometallic complexes, .e.g., the N,N'-alkyl-1, 1-alkylsilylamino metal complexes, can be employed as potential precursors to make thin metal or metal oxide films via either the chemical vapor deposition (CVD) or atomic layer deposition (ALD) method at temperatures less than 500° C. The CVD process can be carried out with or without reducing or oxidizing agents whereas an ALD process usually involves the employment of another reactant such as a reducing agent or oxidizing agent.

These organometallic complexes can be prepared via the reaction of anhydrous divalent metal halides of the formula ($MX_2$) where X preferably is Cl or Br. In a preferred embodiment, $MCl_2$ is reacted with two equivalents of N,N'-alkyl-1,1-alkylsilylamino lithium, $R^1R^2Si(LiNR^3)(NR^4R^5)$. The reaction equation below is representative:

$$MX_2 + R^1R^2Si(LiNR^3)(NR^4R^5) \rightarrow M\{R^1R^2Si(LiNR^3)(NR^4R^5)\} + 2LiX$$

N,N'-alkyl-1,1-alkylsilylamino lithium, $R^1R^2Si(LiNR^3)(NR^4R^5)$, can be prepared by the in situ reaction of an organic compound of the formula ($R^1R^2Si(HNR^3)(NR^4R^5)$) with an alkyl lithium, e.g., $LiBu^n$.

As a preferred method for the formation of thermally stable compounds, it is preferred to choose a ligand having bulky R groups, e.g., $C_{3-4}$ alkyl groups, an aryl group or cyclic group associated with the nitrogen atom These bulky groups aid in the prevention of polymer-like species forming during the reaction. On the other hand, there is a competing issue and that is that the R groups connected to the silicon atom should be as small as possible in order to decrease the molecular weight of the resulting organometallic compound and allow the achievement of complexes having a high vapor pressure. Preferred substituents pendant from the nitrogen atoms are iso-propyl, sec-butyl and tert-butyl groups and methyl or methoxy groups are the preferred substituents connected to the silicon atom.

A wide variety of solvents can be used for the reaction. A polar solvent such as tetrahydrofuran (THF) is recommended due to the poor solubility of the metal halides in the reaction medium. The resulting complexes are usually highly soluble in hydrocarbon solvents such as hexanes. Thus, it is easy to separate the resulting complexes from the reaction mixture by removing the reaction solvents, extraction with hexanes and filtration.

The following examples illustrate the preparation of the N,N'-alkyl-1,1-alkylsilylamino metal complexes as well as their use as precursors in film deposition processes.

EXAMPLE 1

Synthesis of bis(N,N'-di(tert-butyl)-1,1-dimethylsilylamino)cobalt(II)

15 g (0.116 mol) of anhydrous $CoCl_2$ was loaded in a 1 L Schlenk flask with 100 ml THF. To this flask was added $Me_2Si(LiNBu^t)(HNBu^t)$ prepared in situ by the reaction of $Me_2Si(HNBu^t)_2$ (49.5 g, 0.245 mol) with a 2.5 M $LiBu^n$ hexane solution (98 mL, 0.245 mol) in 200 mL of hexanes. The mixture was stirred at room temperature over night. After the reaction was complete, all volatiles were then removed under vacuum, and a dark solid formed by the reaction was extracted with a mixture of hexanes (200 ml). The hexanes extract was filtered through a glass frit with a pad of Celite to afford a dark blue solution. The solution was concentrated to about 50 mL and kept at −40° C. to afford dark crystals. 20 g of the crystals was collected and dried under vacuum. 5 g more of dark crystals was obtained by concentrating the mother solution to about 10 mL.

The yield is 84% on the basis of cobalt. Ana. Calcd for C20H50Co N4 Si2: Co, 12.76; C, 52.02; N, 12.13; H, 10.91. Found: Co, 13.20; C, 49.52; N, 11.44; H, 9.72.

A dark blue crystal of bis(N,N'-di(tert-butyl)-1,1-dimethylsilylamino)cobalt(II) was structurally characterized by X-ray single crystal analysis. The structure below shows cobalt is coordinated with two N,N'-di(tert-butyl)-1,1-dimethylsilylamino ligands in a distorted tetrahedral environment. The average Co—N distance is 2.006 Å.

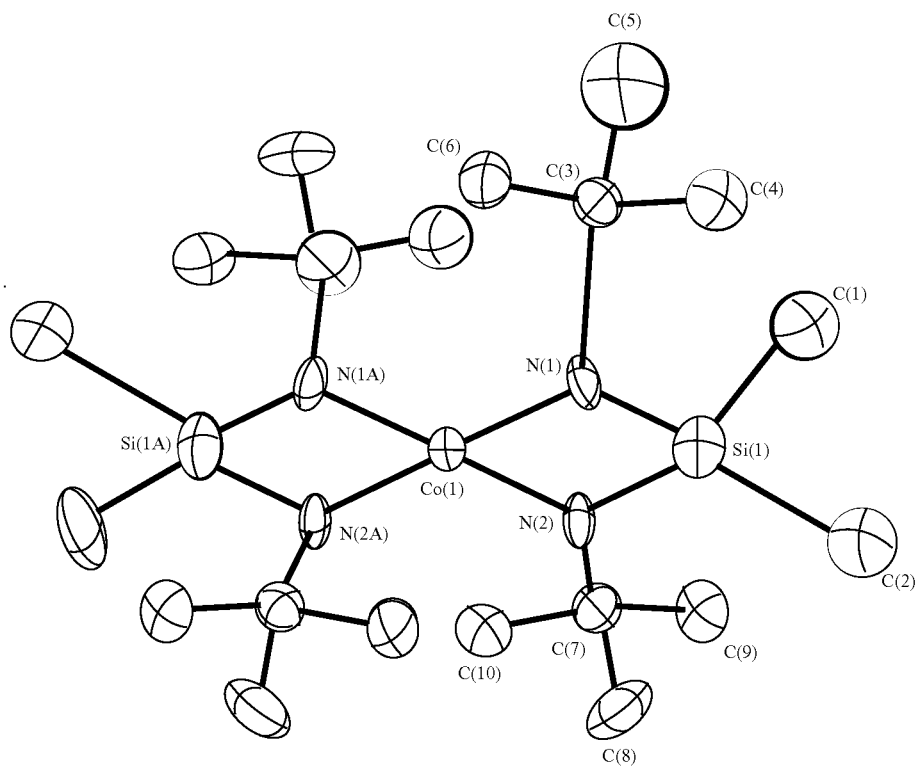

The above represents the crystal structure of bis(N,N'-di(t-butyl)-1,1-dimethylsilaneaminato)Cobalt(II)

The numbers around the atoms are from X-ray single crystal structure analysis.

EXAMPLE 2

Synthesis of Bis(N,N'-di(tert-butyl)-1,1-dimethylsilylamino)nickel(II)

The procedure of Example 1 was followed except that $NiCl_2$ was substituted for $CoCl_2$. 10 g (0.077 mol) of anhydrous $NiCl_2$ was loaded in a 1 L Schlenk flask with 80 ml THF. To this flask was added $Me_2Si(LiNBu^t)(HNBu^t)$ prepared in situ by reaction of $Me_2Si(HNBu^t)_2$ (32.0 g, 0.154 mol) with 2.5M of $LiBu^n$ hexanes solution (61.6 mL, 0.154 mol) in 200 mL of hexanes. The mixture was stirred at room temperature over night.

All volatiles were then removed under vacuum, and the resulting dark solid was extracted with hexanes (200 ml). The hexanes extract was filtered through a glass frit with a pad of Celite to afford a dark green solution. The solution was concentrated to about 50 mL and kept at –40° C. to afford dark crystals. 25 g of the crystals was collected and dried under vacuum. The yield is 70% on the basis of nickel.

A dark green crystal of bis(N,N'-di(tert-butyl)-1,1-dimethylsilylamino)nickel(II) was structurally characterized by X-ray single crystal analysis. The structure below shows the structure in which nickel is coordinated with two N,N'-bis(tert-butyl)-1,1-dimethylsilylamino ligands in a distorted tetrahedral environment. The average Ni—N distance is 2.005 Å. The structure of bis(N,N'-di(tert-butyl)-1,1-dimethylsilylamino)nickel(II) is represented as follows:

EXAMPLE 3

Synthesis of bis(N,N'-di(tert-butyl)-1,1-dimethylsilylamino)iron(II)

The procedure of Example 1 was followed except that anhydrous $FeCl_2$ was substituted for $CoCl_2$. 10 g (0.079 mol) of anhydrous $FeCl_2$ was loaded in a 1 liter Schlenk flask with 50 ml THF. To this flask was added $Me_2Si(LiNBu^t)(HNBu^t)$ prepared in situ by reaction of $Me_2Si(HNBu^t)_2$ (32 g, 0.158 mol) with 2.5M of $LiBu^n$ hexanes solution (63.1 mL, 0.158 mol) in 200 mL of hexanes. The mixture was stirred at room temperature over night. All volatiles were then removed under vacuum, and the resulting dark solid was extracted with hexanes (200 ml). The hexanes extract was filtered through a glass frit with a pad of Celite to afford a purple solution. The solution was concentrated to about 50 mL and kept at –40° C. to afford dark crystals. 16 g of the crystals was collected and dried under vacuum. The yield is 44% on the basis of iron. Ana. Calcd for C20H50FeN4Si2: Fe, 12.18; C, 52.37; N, 12.22; H, 10.99. Found: Fe, 11.81; C, 52.37; N, 11.29; H, 9.21.

A purple crystal of bis(N,N'-di(tert-butyl)-1,1-dimethylsilylamino)iron(II) was structurally characterized by X-ray single crystal analysis. The structure shows Fe coordinated with two N,N'-bis(tert-butyl)-1,1-dimethylsilylamino ligands in a distorted tetrahedral environment. The average Fe—N distance is 2.048 Å.

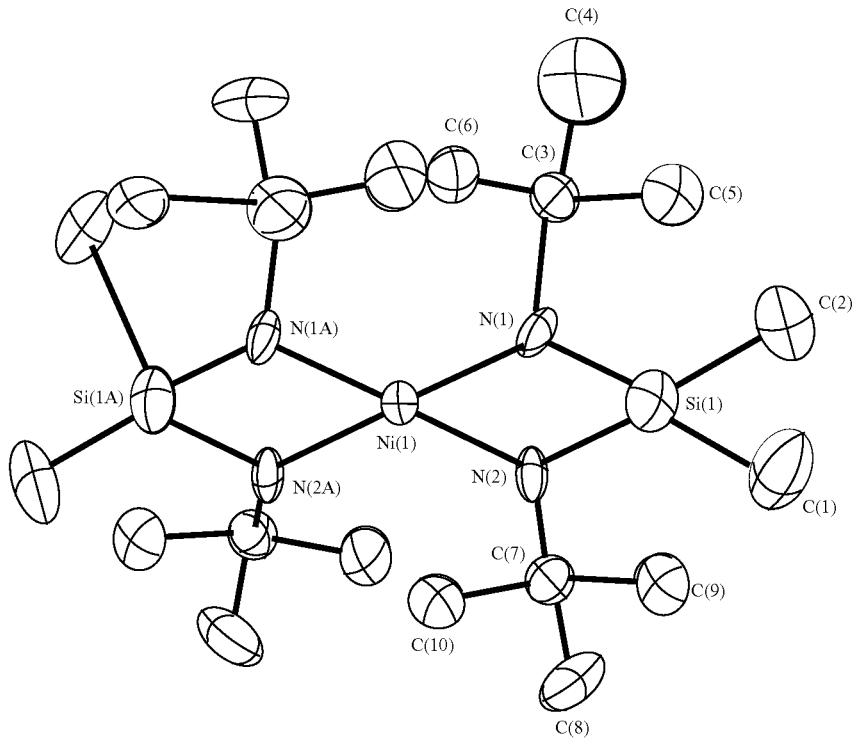

Crystal Structure of (N,N'-di(tert-butyl)-1, 1-dimethylsilylamino)nickel(II)
from X-ray single Crystal Structure Analysis

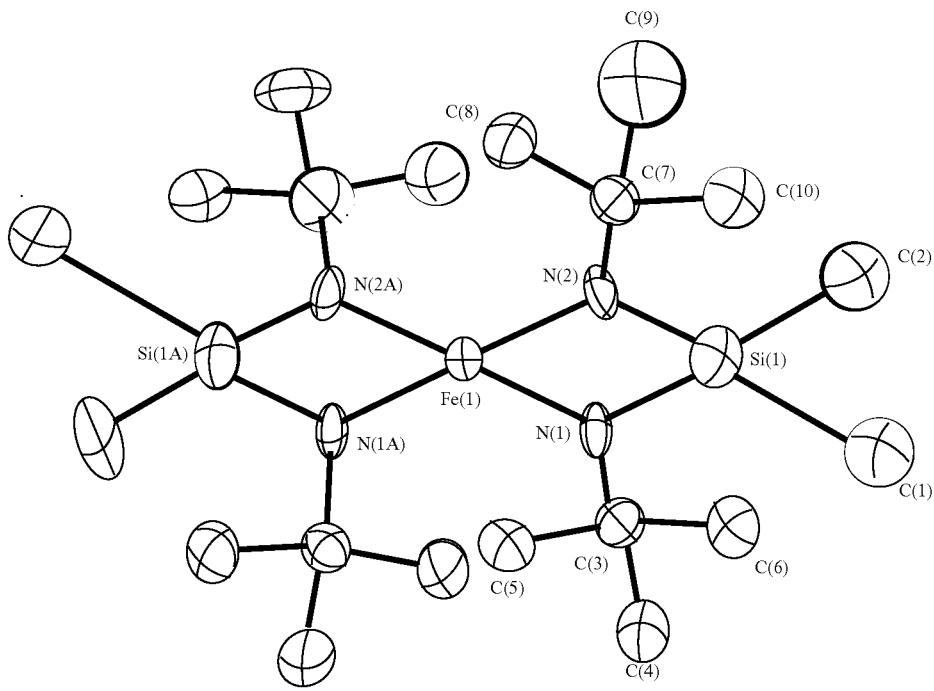

Crystal Structure of Bis(N,N'-di(t-butyl)-1,1-dimethylsilaneaminato)iron(II)
from X-ray Single Crystal Structure Analysis

EXAMPLE 4

Synthesis of bis(N,N'-di(iso-propyl)-1,1-dimethylsilylamino)cobalt(II)

5 g (0.0385 mol) of anhydrous $CoCl_2$ was loaded in a 500 mL Schlenk flask with 50 ml THF. To this flask was added $Me_2Si(LiNBu^t)(HNBu^t)$ prepared in situ by reaction of $Me_2Si(HNBu^t)_2$ (14.2 g, 0.0815 mol) with 2.5M of $LiBu^n$ hexanes solution (32.6 mL, 0.0815 mol) in 100 mL of hexanes. The mixture was stirred at room temperature overnight. All volatiles were then removed under vacuum, and the resulting dark solid was extracted with hexanes (100 ml). The hexanes extract was filtered through a glass frit with a pad of Celite to afford a dark blue solution. The solution was concentrated to about 10 mL and kept at −40° C. to afford dark crystals. 10 g of the crystals was collected and dried under vacuum. The yield is 64% on the basis of cobalt.

EXAMPLE 5

CVD of Bis(N,N'-di(tert-butyl)-1,1-dimethylsilylamino)cobalt(II)

In this example, bis(N,N'-di(tert-butyl)-1,1-dimethylsilylamino)cobalt(II) was used as the organometallic precursor for the formation of films in a conventional CVD apparatus using known CVD techniques to produce a metal silicide film on silicon substrates.

In this embodiment, bis(N,N'-di(tert-butyl)-1,1-dimethylsilylamino)cobalt(II) was vaporized in a bubbler at 90° C. and transported into a CVD chamber in combination 100 sccm $N_2$ carrier gas. The CVD chamber was a cold-wall system having a heated substrate holder. The substrate was maintained at 400° C. and the chamber pressure was maintained at 1 Torr. EDX analysis of the resulting films indicated the films contained cobalt.

Summarizing from the description and examples, N,N'-alkyl-1,1-alkylsilylamino metal complexes of the general formula $M\{R^1R^2Si(NR^3)(NR^4R^5))\}_2$ may be used for forming a metal or metalloid oxide on a substrate including that of forming a glue layer between copper and diffusion barrier such as TaN, TiN, WN, TaSiN, TiSiN, WSiN in an electronic device such as employed in the fabrication of solid state transistors, capacitors, vias, and circuits. One may contact the N,N'-alkyl-1,1-alkylsilylamino metal complex with or without reducing agents (i.e., hydrogen, hydrazine, monoalkylhydrazine, dialkylhydrazine, ammonia and mixtures thereof). Oxygen containing reactants may be introduced to the deposition chamber as desired and examples include water, $O_2$, $H_2O_2$ and ozone. Preferably, an ALD process is employed for the deposition of the N,N'-alkyl-1,1-alkylsilylamino metal complex over a CVD process simply because of the self-limiting nature of ALD process. Thin films formed by ALD allows for the generation of 45 nm films and below.

The invention claimed is:

1. An organometallic complex represented by the structure:

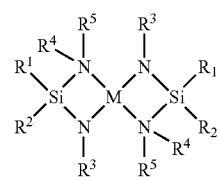

wherein M is a metal selected from the group consisting of Group VIIb, VIII, IX and X, and $R^{1-5}$ can be same or different selected from the group consisting of hydrogen, alkyl, alkoxy, fluoroalkyl, fluoroalkoxy, cycloaliphatic, and aryl.

2. The organometallic complex of claim 1 wherein M is selected from the group consisting of cobalt, iron, nickel, manganese, ruthenium, zinc, copper, palladium, platinum, iridium, rhenium, and osmium.

3. The organometallic complex of claim 2 wherein $R^{1-5}$ is selected from the group consisting of hydrogen and alkyl.

4. The organometallic complex of claim 1 having the chemical name, bis(N,N'-di(tert-butyl)-1,1-dimethylsilylamino)cobalt(II).

5. The organometallic complex of claim 1 having the chemical name, bis(N,N'-di(tert-butyl)-1,1-dimethylsilylamino)iron (II).

6. The organometallic complex of claim 1 having the chemical name, bis(N,N'-di(tert-butyl)-1,1-dimethylsilylamino)nickel (II).

7. In a deposition process for forming conformal metal or metal oxide thin films on a substrate wherein an organometallic precursor is charged to a deposition chamber, vaporized and deposited on a substrate, the improvement which comprises the use of the organometallic complex of claim 1 as said organometallic precursor.

8. The deposition process of claim 7 wherein the deposition process is a chemical vapor deposition process.

9. The deposition process of claim 7 wherein the deposition process is an atomic layer deposition process.

10. The deposition process of claim 7 wherein the organometallic complex is represented by the formula:

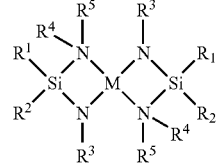

wherein M is a metal selected from the group consisting of iron, nickel, cobalt, and copper, $R^1$ and $R^2$ are independently methyl or methoxy and $R^3$, $R^4$ and $R^5$ are independently selected from the group consisting of iso-propyl, sec-butyl and t-butyl.

11. The deposition process of claim 7 wherein a reducing agent is introduced to the deposition chamber after the introduction of said organometallic precursor to produce metal thin film.

12. The process of claim 11 wherein the reducing agent is selected from the group consisting of hydrogen, hydrazine, monoalkylhydrazine, dialkylhydrazine, ammonia and mixtures thereof.

13. The deposition process of claim 12 wherein the process is a chemical vapor deposition process.

14. The deposition process of claim 12 wherein the process is an atomic layer deposition process.

15. The deposition process of claim 7 wherein an oxygen containing reactant is introduced to the deposition chamber to prepare metal oxide film.

16. The process of claim 15 wherein the oxygen containing is selected from the group consisting of water, $O_2$, $H_2O_2$, and ozone.

17. A method of forming an organometallic complex having the structure:

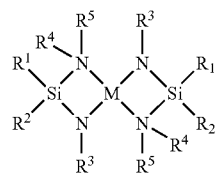

which comprises:
reacting a metal halide of the formula $MX_2$ wherein M is a metal selected from the group consisting of Group VIIb, VIII, IX and X, and X is Cl or Br with two equivalents of a silyl compound of the formula, $R^1R^2Si(LiNR^3)(NR^4R^5)$ wherein $R^{1-5}$ can be the same or different and selected from the group consisting of hydrogen, alkyl, alkoxy, fluoroalkyl and alkoxy, cycloaliphatic, and aryl.

18. The method of claim 17 wherein M is a metal selected from the group consisting of iron, nickel, and cobalt, copper.

19. The method of claim 18 wherein $R^1$ and $R^2$ are methyl or methoxy and $R^3$, $R^4$ and $R^5$ are selected from the group consisting of iso-propyl, sec-butyl and tert-butyl.

20. The method of claim 15 wherein the resulting metal oxide film can be reduced to metal film via a reducing agent selected from the group consisting of hydrogen, hydrazine, monoalkylhydrazine, dialkylhydrazine, ammonia and mixtures thereof.

* * * * *